United States Patent [19]

Yewer, Jr.

[11] Patent Number: 5,036,864
[45] Date of Patent: Aug. 6, 1991

[54] TORQUE RING FOR BELT

[76] Inventor: Edward H. Yewer, Jr., 6251 N. Highway 83, Hartland, Wis. 53029

[21] Appl. No.: 535,245

[22] Filed: Jun. 8, 1990

[51] Int. Cl.$^5$ .......................... A61F 5/37; A61F 5/02; A41F 3/02
[52] U.S. Cl. ...................................... 128/876; 128/78; 2/338
[58] Field of Search .................. 128/876, 878, 879, 78; 2/321, 337, 338, 309, 311, 312; 24/163 R, 170, 180, 585; 272/143, 119, 117

[56] References Cited

U.S. PATENT DOCUMENTS

| 402,272 | 4/1889 | Norris | 24/180 |
|---|---|---|---|
| 475,951 | 5/1892 | Stahley | 24/180 |
| 844,540 | 2/1907 | Roy | 24/170 |
| 857,864 | 6/1907 | Bowyer | 24/180 |
| 939,902 | 11/1909 | Garrison | 24/163 R |
| 3,011,237 | 12/1961 | Prete, Jr. | 24/170 |
| 3,063,447 | 11/1962 | Kirsten | 128/876 |
| 4,528,700 | 7/1985 | Johnston | 2/338 |
| 4,545,370 | 10/1985 | Welsh | 2/338 |
| 4,782,535 | 11/1988 | Yewer et al. | 2/321 |

FOREIGN PATENT DOCUMENTS 2539596  7/1984  France .............................. 24/163 R Primary Examiner—Robert A. Hafer
Assistant Examiner—Michael Brown
Attorney, Agent, or Firm—Quarles & Brady

[57] ABSTRACT

A belt with a cinching device including a torque ring surrounding a tightening strap. The torque ring loosely receives a free end of the strap, the opposite end being fastened to a retaining buckle. The free end of the strap may be pulled in a reverse direction against the retention forces of the torque ring, in contrast to conventional tensile forces being applied. This permits minimal movement of the strap in a reverse direction while being clamped in place or otherwise retained by cooperating elements of the buckle. The torque ring is further adapted to releasably, retain a buckle tongue member in clamping engagement with the strap to prevent accidental opening of the buckle.

8 Claims, 1 Drawing Sheet

TORQUE RING FOR BELT

This application is a continuation of application Ser. No. 07/309,180, filed Feb. 13, 1989 now abandoned.

BACKGROUND OF THE INVENTION

1. Field of the Invention

This invention pertains to a means for tightening or cinching a belt strap, and in particular, relates to a so-called "torque ring" for the belt strap having a triple purpose of assisting in tightening the belt strap when using a cam-type buckle, as a loop for retaining a free end of the belt strap after tightening and so a retainer for the free end of a buckle tongue to hold it in closed position. The torque ring has particular applicability to weight lifting and for motorcycle or truck driving body support.

2. Description of Related Art

Prior belts or binders utilizing cam-type buckles for releasably retaining opposite ends of a belt strap encircling a human, animal or other object to be tightly encircled by the belt and strap were limited in the degree of attainable "tightness". For instance, although the present invention has application to any of several types of belts, a particular application may be found in belts such as the type described in U.S. Pat. No. 4,782,535 granted to Yewer et al. on Nov. 8, 1988. In that patent, there are disclosed two usual-type belt loops surrounding a supporting webbing or strap in the usual manner. The loops were supplied for retaining the free end of the webbing or strap after it has been passed through a conventional cam-type buckle.

OBJECTS AND SUMMARY OF THE INVENTION

A general object of the present invention is to provide means for assisting and insuring tightness of a belt having a cam-operated buckle as the belt encircles an object, such as the waist of a human being.

It is a particular object of the present invention to provide a torque ring to be used in conjunction with a cam-operated belt buckle or other types of buckles providing necessary cinching action, wherein the free end of an elongated belt may be threaded through the camming portion of the buckle and through the torque ring and pulled in a reverse direction towards the tongue of the buckle as the tongue is moved into camming, clamping relationship with the free end and the buckle end of the belt.

It is another object of the present invention to provide cinching means for assisting and insuring full tightness of a free end of a belt with respect to a buckle end of a belt with the belt encircling an object and whereby the free end may be held in a tightened position during and after closure of the belt buckle. The torque ring of this invention may be used with a buckle comprising a conventional channel-member having oppositely disposed upright sides for retaining a web against the base of the support. The locking tongue is disposed between the upright side walls and retained in place by means of a pivot member. The tongue is L-shaped and may have teeth at the relatively short base of the L-shaped member. These teeth engage the free end of the webbing that is threaded between the base of the tongue and the base of the support. After threading to a predetermined tightening position, the pivotable tongue is then moved to closed position relative to the support. It will be apparent that as soon as the teeth engage the web they will tend to force the web longitudinally in a reverse direction because of the pivoted camming action and for the distance between the initial touching position of the teeth to the final closed position of the tongue member.

The present invention further provides a temporary restraining means which opposes the "reverse" directional forces tending to loosen the belt from a desired position with respect to the embraced or encircled object. It will become immediately important that in the matter of weight lifting and for body support in a human being, that tight contact is not only desired, but often necessary. It will also be apparent that such cinching action is also very desirable when saddling a horse, use as a windsurfing harness, or for other similar activity requiring as tight an embrace as possible.

These and other objects and advantages which are attained by the invention will become more fully apparent as the description which now follows is read in conjunction with the accompanying drawing.

DETAILED DESCRIPTION OF THE INVENTION

Figure 1:
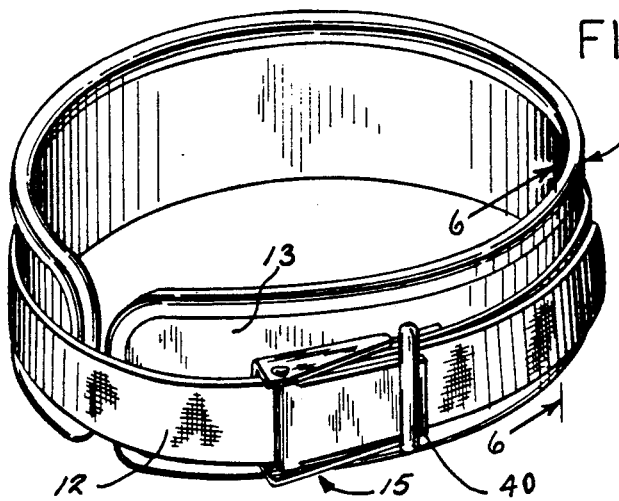
FIG. 1 is a perspective view of a belt and belt strap including a torque ring constructed in accordance with the present invention.
Figure 2:
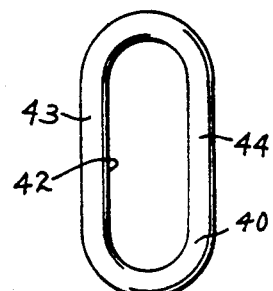
FIG. 2 is a front elevational view illustrating the torque ring of the present invention in detail.

Referring to the drawings, there is indicated generally at 10 a supporting belt or binder to which the present invention may be applied. This belt or binder has been described and claimed in the aforementioned U.S. Pat. No. 4,782,535.

A supplemental webbing strap 12 of approximately 2 inches in width is coextensive of the belt body 13 and extends beyond the length of the body 13 as required. The webbing 12 is sewn to the body 13 intermediate its end portions and is preferably provided with adjustable tightening and clamping means in the form of the cam-type buckle shown generally at 15. With respect to FIGS. 3 and 4, it will be observed that the buckle 15 is of general U-shape and comprises a flat base 16 having oppositely disposed, upstanding, integrally formed sidewalls 17. A manually operated locking tongue 20 is pivotally supported between the upstanding sidewall 17 by means of a transverse pivot pin 22 supported at its ends by the respective sidewalls 17.

Figure 5:
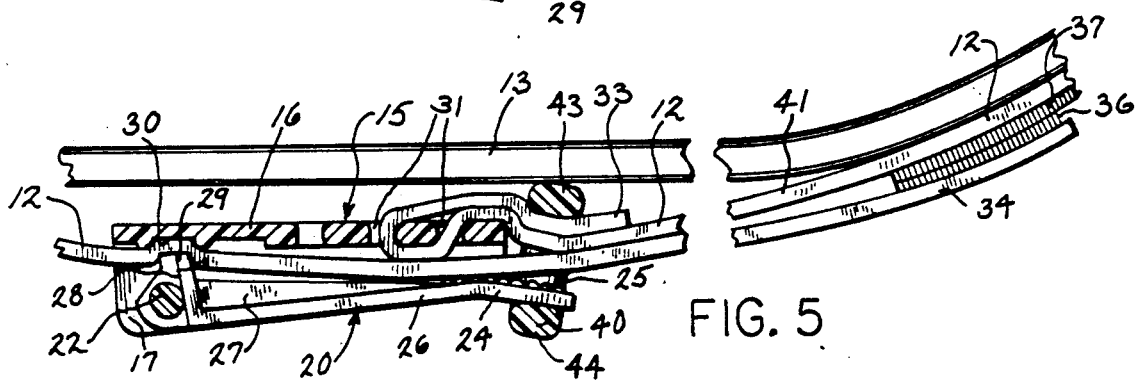
FIG. 5 is a top fragmentary view of a belt and a closure combination similar to the view of FIG. 4, but with all elements in clamping relationship.

The molded tongue 20 is preferably provided with an outwardly bent portion 24 having finger-engaging ridges 25 or other frictional surface engaging configuration on the inner side thereof and extending inwardly of a portion of the tongue 20. The body portion 26 of the tongue 20 is also preferably provided with strengthening integrally molded webs 27. The body portion of the generally L-shaped tongue 20 terminates in an angularly upstanding clamping portion 28 preferably including strap clamping teeth 29. The teeth 29 along with the integrally molded transverse ridge 30 of the base 18 acts to clamp the webbing strap 12 between the teeth 29 and the transverse groove 30 when the tongue 20 has been pivoted to closed position as shown in FIG. 5. Also with reference to FIG. 5, it will be noted that the base 16 of the buckle 15 contains two transverse slots 31 for receiving and retaining one end 33 of the webbing strap 12. The end 33 is threaded through the slots as shown and bent backwardly upon itself to be sewn or otherwise fastened to the body of the webbing strap 12.

Figure 6:
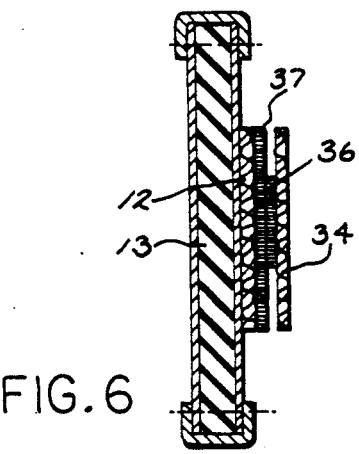
FIG. 6 is a cross-sectional view taken along line 6—6 of FIG. 1.

The free end 34 of the strap 12 also preferably contains one portion 36 of a Velcro fastener engageable with a cooperating portion 37 (see FIG. 6) for retention of the free end 36 to the body of the strap 37.

The present invention focuses on a novel torque ring 40 freely slideable on the strap 12 and of internal dimensions suitable for receiving the free end portion 34 of the strap 12, and when fully closed, the outwardly bent portion 24 of the buckle 20 as shown in FIG. 5 is provided with a pair of elongate legs 43 and 44. Leg 43 abuts the interior surface of the free end portion 41 of the strap 12, and the leg 44 abuts the exterior surface of the free end portion 34. The torque ring 40 has an internal dimension at least slightly smaller than the outer dimensions of the buckle 15 so as to be retained between the buckle 15 and the end portion 33 of the webbing strap 12. It is preferred to sew the remaining areas of the strap webbing 12 directly to the body 13 of the belt or binder 10.

The torque ring is of sufficient internal dimension to define an opening 42 to readily accept both ends 33, 34 of the strap webbing 12, with the particular purpose of assisting in tightening the belt strap 12 around an object encircled by the belt 10 to the full desired extent, and without slippage in a return or reverse direction, as is usually the case when using cam-type buckles. This function will no be described.

Figure 3:
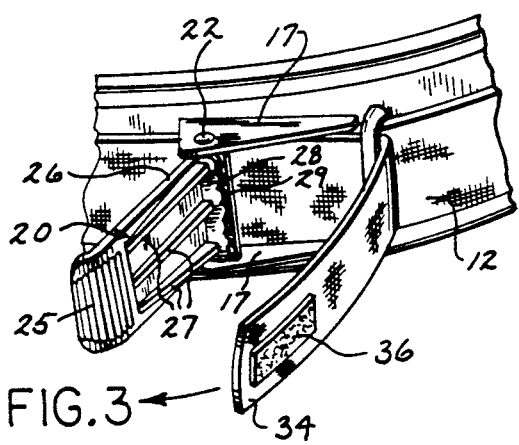
FIG. 3 is a fragmentary perspective view illustrating the cooperating components of the present invention.
Figure 4:
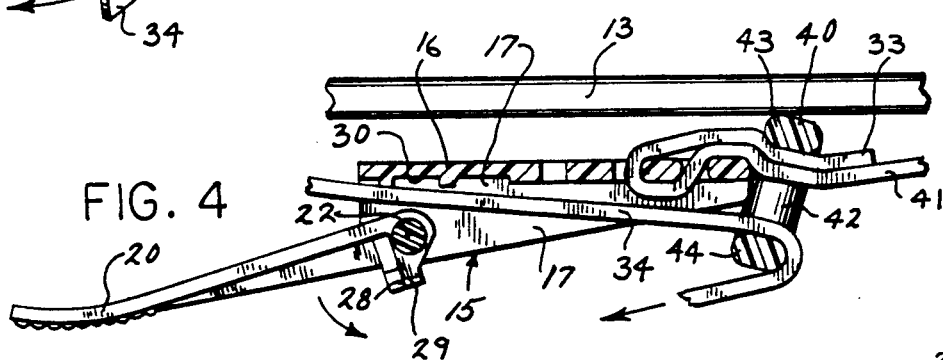
FIG. 4 is a top plan view, partly in section, illustrating the relationship of the cooperating elements prior to closure of a cam-type buckle.

With attention first being directed to the views of FIGS. 3 and 4, it will be observed that the free end 34 of the webbing strap 12 is fed through the opening existing between the pivot end of the tongue 20 and the base 16 of the buckle 15, and then through the opening 42 of the torque ring 40. The distal portion of the free end 34 is then pulled to the left with respect to FIG. 4 until the webbing strap 12 has been drawn to the desired degree of tightness for the encircling belt 10 around its encircled object, such as the waist of a human being. Tension is continued on the free end 34 while the other hand of the person tightening or fastening the belt operates the manually operable tongue 20 of the buckle 15 and rotates it on its pivot pin 22 to the final locking position shown in FIG. 5. In the position of FIG. 5, it will be noted that the teeth 29 of the clamping portion 28 will force the free end 34 into the cavity or groove formed by the transverse ridge 30 in a "snap-over" type camming movement. The buckle 15 and tongue 20 are then held tightly in clamping engagement with the free end 34 of the strap 12. The torque ring 40 may be slipped over the outwardly bent portion 24 to retain the ring 40 in place relative to the outward bias of the relatively resilient tongue 20 to maintain buckle in locking position.

The locking aspect is important to keep from accidental openings as the belt is used in many active sports where an unexpected fall may open buckle—water skiing—snow skiing—windsurfing.

Also when weight lifting the wearer might otherwise brush the members with his or her hand or may rub against equipment.

It will be apparent that with continued tension being applied to the free end 34 in the direction of the arrows of FIG. 4, the leading engaging members will be held against the torqueing action of the torque ring 40, while the camming action of the body 20 of the buckle 15 acts against the free end portion 34 to retain the same in the groove 30 of the buckle 15, thereby wedging the strap 12 between the base 16 of the buckle 15 and the teeth 29 of the tongue 20. The tension bias exerted against the torque ring 40 will permit only locking position with minimal rearward movement of the portion 34 during this locking-clamping action.

To complete the procedure, the free end 34, after being clamped in place against the buckle body 18, is then secured to the strap 12 by means of the Velcro portions 36, and 37.

While a preferred embodiment of the present invention has been illustrated in detail, it is apparent that modifications and adaptations of that embodiment will occur to those skilled in the art. For instance it is within the scope of this invention to utilize the torque ring in connection with conventional belts or belt straps having longitudinally spaced apertures for receiving a tongue-like member protruding through a selected aperture and resting, at its distal end, against a transverse bar end portion of the buckle. Further, the strap 12 may comprise a pair of separate fastening portions each having an end secured to the belt by sewing, stapling or other fastening means and with the respective free ends of the pair being arranged for joining and tightening the belt. It is to be expressly understood that such modifications and adaptations are within the spirit and scope of the present invention as set forth in the following claims:

What is claimed is:

1. A belt for cinching around a body, comprising:
    (a) a strap for surrounding at least a portion of said body to be cinched by the belt, said strap having a first end portion with a free end and having a second end portion with a free end, said end portions being adapted to be brought together to encircle the body;
    (b) a buckle having a frame and a releasable securing means, said frame being secured to the free end of the first end portion of said strap at a first end of the buckle and said releasable securing means being arranged to releasably secure the free end of the second end portion to a second end of the buckle; and
    (c) a torque ring surrounding the first end portion of the strap inwardly of said buckle and having an inside surface at its interior periphery and a far side surface at its periphery which is distal from the buckle, the free end of the second end portion of the strap being insertable through the buckle and through the torque ring; and
    (d) means bridging the inside and far side surfaces of the torque ring in an arc for conveying the second end portion of the strap from a circumferential direction, said circumferential direction being through the torque ring and buckle, to a chordal direction, said chordal direction being away from the body, as the second end portion is moved under tension outwardly away from said body along said chordal direction to tighten the belt around the body.

2. The belt of claim 1, wherein the frame of the buckle has a pivot support at the second end of the buckle and the releasable securing means includes a tongue which is pivoted to the pivot support, said torque including a laterally projecting portion which clamps the strap between the tongue and the frame when the tongue is pivoted toward the torque ring.

3. The belt of claim 2, wherein an end of the tongue is received in the torque ring when the belt is secured around a body.

4. The belt of claim 3, wherein the end of the tongue extends beyond the first end of the buckle and can be received in the torque ring when the belt is secured around a body.

5. The belt of claim 4, wherein the end of the tongue is outwardly-tuned to hook inside the torque ring and orient the torque ring so as to retain the tongue in the secured position.

6. The belt of claim 1, wherein the torque ring has an internal peripheral dimension which is smaller than the buckle so as to restrict longitudinal movement of the torque ring past the buckle during tensioning of the belt around a body.

7. The belt of claim 1, wherein the means bridging the inside and far side surfaces of the torque ring comprises a surface having a finite radius joining said inside and far side surfaces so that said second end portion is freely slideable relative to the torque ring over said surface and past said inside and far side surfaces upon tightening of the belt around a body.

8. The belt of claim 1, wherein the torque ring further has an outside surface and the outside surface is joined to the far side surface with a radius.

* * * * *

UNITED STATES PATENT AND TRADEMARK OFFICE
CERTIFICATE OF CORRECTION

PATENT NO. : 5,036,864

DATED : August 6, 1991

INVENTOR(S) : Edward H. Yewer, Jr.

It is certified that error appears in the above-identified patent and that said Letters Patent is hereby corrected as shown below:

In column 3, line 39, change "will no" to --will now--.

In claim 5, column 5, line 18, change "outwardly-tuned" to --outwardly-turned--.

In claim 8, column 6, line 15, change "claim 1" to --claim 7--.

Signed and Sealed this

Second Day of March, 1993

Attest:

STEPHEN G. KUNIN

*Attesting Officer*     Acting Commissioner of Patents and Trademarks